United States Patent [19]

Sugimoto et al.

[11] Patent Number: 4,897,306

[45] Date of Patent: Jan. 30, 1990

[54] MEDIUM FOR ELECTROPHORESIS

[75] Inventors: Naohiko Sugimoto; Daijiro Nishio; Elichi Hasegawa, all of Asaka, Japan

[73] Assignee: Fuji Photo Film Co., Ltd., Kanagawa, Japan

[21] Appl. No.: 40,486

[22] Filed: Apr. 20, 1987

[30] Foreign Application Priority Data

Apr. 19, 1986 [JP] Japan ................................... 61-90622
Apr. 19, 1986 [JP] Japan ................................... 61-90623

[51] Int. Cl.$^4$ .................... B32B 27/08; C08L 5/00; C08L 5/12; G01N 31/00
[52] U.S. Cl. ..................................... 428/336; 428/339; 428/483; 428/548; 428/520; 428/412; 428/510; 526/303.1; 204/182.8
[58] Field of Search ............... 428/336, 339, 518, 520, 428/483, 412, 510

[56] References Cited

U.S. PATENT DOCUMENTS

| | | | |
|---|---|---|---|
| 4,048,377 | 9/1977 | Boschetti et al. | 428/483 |
| 4,383,376 | 5/1983 | Numamoto et al. | 428/474.7 |
| 4,548,869 | 10/1985 | Ogawa et al. | 428/483 |
| 4,548,870 | 10/1985 | Ogawa et al. | 428/483 |
| 4,631,235 | 12/1986 | Biale | 428/518 |

Primary Examiner—P. C. Ives
Attorney, Agent, or Firm—Jules E. Goldberg

[57] ABSTRACT

An improvement of a medium for electrophoresis which comprises a support of a plastic material and an aqueous polyacrylamide gel, wherein a resin layer comprises a resin having an oxygen permeability coefficient lower than that of the plastic material of the support is arranged betwen the support and the polyacrylamide gel. The resin preferably shows an oxygen permeability of not more than 15 cc/m$^2$·atm·day in the form of a resinous layer of 20 μm thick, and exemplified by a vinylidene chloride-vinyl chloride copolymer, polyvinyl alcohol, polyacrylonitrile, polyvinylidene chloride, a vinyl alcohol-ethylene copolymer, a vinylidene chloride-acrylonitrile copolymer, and an acrylonitrile-methyl acrylate-butadiene copolymer.

8 Claims, No Drawings

MEDIUM FOR ELECTROPHORESIS

BACKGROUND OF THE INVENTION

1. Field of the invention

This invention relates to a medium for electrophoresis, and more particularly relates to a medium for electrophoresis suitably employable for analysis of biopolymers such as proteins, as well as for determination of base sequence of DNA, RNA, their fragments, and their derivatives.

2. Description of prior arts

For the analysis of biopolymers such as proteins, or for determination of base sequence of DNA or RNA, electrophoresis can be carried out in the following manner.

A membrane medium for electrophoresis prepared by coating or casting a membrane-forming material such as agar, cellulose, cellulose acetate, starch, silica gel or polyacrylamide gel over a support such as a glass plate or a transparent plastic sheet (or film) is impregnated with a buffer solution; on the medium is applied a substance to be analyzed (sample); the applied sample is developed (or resolved) on or in the medium by applying a voltage between the both ends of the support, and then the developed substance is dyed thereon; and then the dyed sample is measured on the optical density to quantitatively determine the developed components of the sample.

Details of the electrophoresis and medium therefor are given in "Experimental Text for Electrophoresis (5th revision)" edited by Electrophoresis Society of Japan (Bunkodo, 1975), "Modern Electrophoresis" edited by Aoki & Nagai (Hirokawa Shoten, 1973), etc.

Recently, the electrophoresis has been frequently employed to analyze substances originating from a living body; for instance, the analyses of proteins originating from a living body are generally performed in the course of biochemical analysis for diagnosis. The determinations of base sequences of DNA or RNA are also performed in the course of the study in the genetic engineering technology.

As the membrane or sheet for electrophoresis, a filter paper was previously employed, but recently an agarose membrane or a polyacrylamide gel membrane (or medium) has been employed from the viewpoints of their advantageous properties. Particularly, the polyacrylamide gel membrane showing a molecular sieve function is widely employed recently. More particularly, in the method for determination of base sequence of DNA, RNA, their fragments, and their derivatives according to the post-label method, a procedure of slab electrophoresis using a polyacrylamide gel membrane has become essential.

The polyacrylamide gel membrane is prepared by crosslinking polymerization of a monomer such as acrylamide and a two-functional crosslinking agent such as N,N'-methylenebisacrylamide under an oxygen-free condition in the presence of water and a polymerization catalyst.

In the course of the preparation of the polyacrylamide gel membrane, a modifier such as an anionic surfactant, urea or formamide may be incorporated into the membrane. When only a small amount of the modifier is required for the preparation of the gel membrane for protein analysis, the modifier can be incorporated into the membrane by applying an aqueous modifier solution onto the wet gel membrane or immersing the gel membrane in an aqueous modifier solution.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3–1 mm); sealing the gel-forming solution from oxygen; and causing the crosslinking polymerization to prepare the desired gel membrane.

The polyacrylamide gel membrane prepared as above is employed for electrophoresis. For example, the electrophoresis for determination of base sequence of DNA is performed in the manner such as described below.

The polyacrylamide gel membrane is vertically placed in the form of being sandwiched between the glass plates, and in the first place a pre-electrophoresis procedure is carried out. Then, a certain amount of a sample (e.g., $^{32}$P-labeled DNA cleaved by Maxam-Gilbert method) is introduced into sample slots provided on the membrane, and electrophoresis is carried out. After the electrophoresis is carried out for a certain period of time (e.g., approx. 6–12 hours), one glass plate is removed carefully. Then, the exposed gel membrane is covered with a polymer film such as a poly(vinylidene chloride) film and subjected to the autoradiographic process. The autoradiographic process is carried out by the following procedures: A radiographic film and an intensifying screen are superposed in layers on the film covering the gel membrane, whereby exposing the radiographic film to the gel membrane at a low temperature (e.g., −80° C.) for a certain period of time (e.g., approx. 10–20 hours). After the exposing procedure, the radiographic film is developed, and the resolved pattern reproduced on the film is studied for determination of the base sequence of DNA, etc.

The above-described conventional polyacrylamide gel membrane is easily breakable, so that it is practically impossible to establish a system of preparing the polyacrylamide gel membrane in a mass scale and supplying technicians of electrophoresis with it in response to their requests. But recently, as more frequently the electrophoresis is employed to analyze substances originating from a living body, demand for polyacrylamide gel membrane has been sharply increased. Thus it is desired to establish the above-described mass-production system.

One of the available methods for preparing a polyacrylamide gel membrane in a mass scale comprises conveying a continuous plastic film at a constant rate, coating thereof a gel forming solution, and radically polymerizing the coated layer in an inert atmosphere (e.g., nitrogen) to form a cross-linked membrane. However, in order to carry out the said method effectively, the rate of forming the gel from the said gel forming solution should be sufficiently high. But, the conventional crosslinking agent which has been used for preparing the polyacrylamide gel membrane hardly meet the above requirement.

SUMMARY OF THE INVENTION

An object of the present invention is to provide a medium for electrophoresis which is suitably employable for analysis of biopolymers such as proteins or DNA.

Another object of the invention is to provide a medium for electrophoresis which can be prepared in a mass scale.

A further object of the invention is to provide a lightweight medium for electrophoresis using a plastic support and showing a resolving power similar to that of the conventional medium for electrophoresis using a glass support.

There is provided by the present invention a medium for electrophoresis which comprises a support of a plastic material and an aqueous polyacrylamide gel formed by crosslinking polymerization of an acrylamide compound and a crosslinking agent in the presence of water, the improvement wherein a resin layer comprising a resin having an oxygen permeability coefficient lower than that of the plastic material of the support is provided between the support and the aqueous polyacrylamide gel.

Since the medium for electrophoresis according to the present invention has on the support a resin intermediate layer which reduces permeation and diffusion of oxygen to an aqueous polyacrylamide gel to be arranged thereof. Accordingly, the crosslinking reaction for the formation of the electrophoretic medium layer (i.e., aqueous polyacrylamide gel layer) proceeds very smoothly and quickly, as compared with on the conventional medium for electrophoresis using a plastic support but having no such oxygen-permeation preventive layer. Thus, the medium for electrophoresis of the invention shows almost the same electrophoretic characteristics as the conventional medium for electrophoresis using a glass support.

DETAILED DESCRIPTION OF THE INVENTION

A medium for electrophoresis of the present invention comprises a plastic support, a resin intermediate, and an aqueous polyacrylamide gel layer, superposed in order.

Examples of the plastic support of the medium for electrophoresis of the invention include various resinous materials in the form of sheet (the term "sheet" includes a film and a plate). Examples of the support of the plastic material sheet employable for the medium for electrophoresis include various polymer materials in the form of sheet. Examples of the polymer materials include polyethylene terephthalate, polycarbonate of Bisphenol A, polyvinyl chloride, vinylidene chloride-vinyl chloride copolymer, polymethyl methacrylate, polyethylene, polypropylene, cellulose acetates, and cellulose acetate propionate. Preferred is a polyethylene terephthalate sheet.

The plastic support preferably has been treated to have increased hydrophilic property on its surface. The treatment can be done by known processes such as irradiation of ultra-violet rays, glow discharge treatment, corona discharge treatment, flame treatment, irradiation of electron beam, chemical etching treatment and electrolytic treatment.

The support generally has a thickness in the range of approx. 50 to 500 $\mu$m, preferably approx. 70 to 300 $\mu$m.

In the preparation of the conventional electrophoresis medium using a plastic support, a coating solution comprising a polyacrylamide gel-forming gel is coated on the support directly or via an adhesive layer, and a crosslinking reaction is caused to proceed under nitrogen atmosphere.

In the electrophoresis medium of the invention, a resinous intermediate layer comprising a resin having an oxygen permeability coefficient lower than that of the plastic material of the support is provided between the plastic support and the aqueous polyacrylamide gel.

The resin of the intermediate layer of the invention preferably has an oxygen permeability of not more than 15 cc/m$^2$·atm·day, more preferably not more than 10 cc/m$^2$·atm·day, in the form of a resinous layer of 20 $\mu$m thick. Examples of the preferred resins include a vinylidene chloride-vinyl chloride copolymer, polyvinyl alcohol, polyacrylonitrile, polyvinylidene chloride, a vinyl alcohol-ethylene copolymer, a vinylidene chloride-acrylonitrile copolymer, and an acrylonitrile-methyl acrylate-butadiene copolymer. The oxygen permeability described herein is a value determined by a generally employed Mocon method.

The intermediate resin layer preferably has a thickness in the range of approx. 0.5 to 20 $\mu$m, more preferably in the range of approx. 1 to 8 $\mu$m.

The composite of the support and the resin layer preferably shows an oxygen permeability of not more than 10 cc/m$^2$·atm·day, more preferably 7 cc/m$^2$·atm·day.

On the intermediate resin layer is formed an aqueous gel layer directly or via other intermediate layer such as an adhesive layer.

The aqueous gel layer is now described in more detail.

The aqueous gel layer (may be referred to herein as "gel membrane") employed in the invention is a layer consisting essentially of an aqueous polyacrylamide gel formed by crosslinking polymerization of an acrylamide compound and a crosslinking agent having at least three reactive groups in the presence of water. On or in the aqueous gel layer, electrophoresis is carried out.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous solution" is used to include both a solution in water as well as a solution in an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl)acrylamide and diacetonacrylamide, as well as methacrylamide and its homologues. These compounds can be employed independently or in combination. Acrylamide is most preferred among these acrylamide compounds, and said acrylamide can be also preferably employed in combination with one or more of other acrylamide compounds.

Known crosslinking agents can be employed singly or in combination in the preparation of the aqueous gel layer. Examples of the crosslinking agents include bifunctional compounds such as N,N'-methylenebisacrylamide (BIS), N,N'-propylenebisacrylamide (PBA), di(acrylamidodimethyl)ether (DAE), 1,2-diacrylamide ethyleneglycol (DEG), ethyleneureabisacrylamide (EDA), N,N'-diallyltartardiamide (DATD) and N,N'-bisacrylylcystamine (BAC), and trifunctional compounds such as triallylcyanurate, triallylisocyanurate, 1,3,5-triacryloylhexahydro-s-triazine. The crosslinking agents are described, for instance, in "Electrophoresis" 1981, 2, 213–228.

The crosslinking agent can be employed in an amount of approx. 1 to 30 wt. %, preferably approx. 3 to 10 wt. %, based on the total weight of the monomer (i.e., acrylamide compound) and the crosslinking agent. The gel concentration preferably is in the range of approx. 3 to 30 wt/v % (total weight of monomer and crosslinking agent per total volume of gel membrane comprising monomer, crosslinking agent and aqueous solvent), the concentration being expressed in accordance with the definition indicated by S. Hjerten in Arch. Biochem. Biophys. 1 (Suppl.), 147 (1962).

The medium for electrophoresis of the invention can be employed for analysis of proteins and conjugated proteins (e.g., lipoproteins, glycoproteins, etc.) and the medium (gel membrane) of the element may comprise an anionic surfactant as a modifier. The use of the anionic surfactant is generally essential or preferable for the electrophoretic analyses of proteins or conjugated proteins, because it favorably contributes to perform separation of the protein and conjugated protein and determination of molecular weight of these proteins. However, the medium for electrophoresis may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion such as sodium ion, potassium ion, or lithium ion. Sodium ion is preferred from the economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for determination of molecular weight thereof. The anionic surfactant (modifier) can be contained in the gel-forming solution in an amount of approx. 0.05 to 2.0 wt/v % (weight per volume of the gel forming solution), preferably approx. 0.1 to 1.5 wt/v %.

The medium for electrophoresis of the invention also can be employed for determination of base sequence of DNA, RNA, their fragments, and their derivatives. For this purpose, a compound containing at least one carbamoyl group is generally incorporated into the electrophoresis medium as a modifier. Examples of the modifier include urea and formamide. Urea is most preferred. The modifier can be used in an amount of approx. 40 to 60 wt. % based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

The gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in the range of approx. 2 to 100 wt. %, preferably, approx. 5 to 50 wt. %, based on the total weight of the monomer and crosslinking agent.

The addition of a water-soluble polymer serves to impart elasticity to the gel membrane, and thus modified gel membrane is still elastic even after it is dried. Thus, the gel membrane is so improved as to be free from brittleness, whereby the gel membrane becomes hardly breakable. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO No. 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel forming solution can be controlled through changing the temperature of the solution, whereby suppressing flowability of the solution as well as facilitating the formation of the gel membrane.

A pH buffer agent can be contained in the gel membrane of the invention.

In the medium for electrophoresis of protein and protein derivatives, a buffer agent which is able to buffer a solution to a range of pH 2.5 to 10.0 can be incorporated. Such buffer agent are described in publications such as "Chemistry Handbook, Fundamental Edition" compiled by The Chemical Society of Japan (Maruzen Ltd., Tokyo, 1966) pages 1312–1320; "Modern Electrophoresis" edited by Aoki and Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroxymethyl)methyl]-3-aminopropanesulfonic acid (TAPS) or its salt. Preferable examples of the buffer agent include potassium dihydrogenphosphate-disodium hydrogenphosphate, Tris-sodium borate, Tris-sodium borate-EDTA·2Na, Tris-citric acid, sodium barbital-sodium acetate, sodium barbital-hydrochloric acid, barbital-sodium barbital, acetic acid-sodium acetate, lactic acid-sodium lactate, citric acid-disodium hydrogenphosphate, Bicine, HEPPSO, sodium salt of HEPPSO, EPPS, sodium salt of EPPS, TAPS, sodium salt of TAPS, etc.

In the medium for electrophoresis of DNA and the like, a buffer agent which is able to buffer a solution to a range of pH 8.0 to 9.0, preferably pH 8.2 to 8.3 can be incorporated. Such buffer agents are described in the aforementioned publications.

Examples of the buffer agent include tris(hydroxymethyl)aminomethane (Tris), N,N-bis(2-hydroxyethyl)-glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt employable in combination with the compounds. Preferable examples of the buffer agent include Tris, boric acid-EDTA·2Na (pH 8.3).

The gel membrane of the invention is formed by radical crosslinking polymerization between the monomer such as acrylamide with the trifunctional compound (i.e., crosslinking agent) in an aqueous medium in which the water-soluble polymer and agarose preferably are dissolved almost homogeneously. Thus obtained gel is assumed to have a structure in which the water-soluble polymer and agarose are dispersed in the three dimensional crosslinked polymer formed by the reaction of the monomer and cross-linking agent, and the water-soluble polymer and agarose dispersed and entangle with the three dimensionally crosslinked polymer structure.

The crosslinking polymerization can be initiated by a known method, for instance, in the presence of a peroxide and/or under irradiation of ultraviolet rays. The reaction can be further accelerated by heat and irradiation with ultraviolet rays.

As the polymerization catalyst, a known low temperature-polymerization initiator such as those described in "Electrophoresis" 1981, 2, 213–219, ibid. 1981, 2, 220–228; and "Modern Electrophoresis" edited by Aoki and Nagai (Hirokawa Shoten, 1973) can be used. Examples of the initiator include a mixture of β-dimethylaminopropionitrile (DMAP) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultraviolet rays. The radical reaction initiator can be employed in the amount of approx. 0.3 to 5 wt. %, preferably approx. 0.5 to 3 wt. %, based on the total amount of the monomer and crosslinking agent.

A polyol compound such as glycerol or ethylene glycol can be contained in the aqueous gel membrane of the invention as a wetting agent. The polyol compound can be introduced in an amount of approx. 5 to 40 wt. % based on the volume of the aqueous gel membrane. Glycerol is particularly preferable among the polyol compounds. The addition of the wetting agent serves to keep the gel membrane from excessive dryness possibly caused by evaporation of water during storage of the medium, whereby preventing the medium from turning brittle or cracking caused by the excessive dryness. Thus, the improvement of physical properties of the gel membrane is accomplished.

The gel membrane of the element of the invention can be prepared by a process in which a gel forming solution is coated by a known method on the intermediate resin layer having a low oxygen permeability. The gel forming solution is then crosslinked to polymerization on the surface of the support. The crosslinking reaction is preferably performed under inert conditions such as nitrogen atmosphere.

In the case the gel forming solution is crosslinked on the surface of the support, the surface of the gel forming solution layer can be covered with a covering material such as a film, sheet, or plate. The same material as employable for the support can be employed as the covering material. The covering materials may be previously so treated by glow discharge treatment to have a hydrophilic surface. The covering material has thickness of not more than 300 μm, and preferably has approx. 4 to 200 μm, from the practical viewpoint. The covering material may have on the surface a resin layer showing a low oxygen permeability which is exemplified by the aforementioned resin layer showing a low oxygen permeability for the support.

In the case that the covering material is thick (e.g., approx. 70 to 300 μm), the element of the present invention can be prepared by the following steps: the gel forming solution is first coated on the covering material and crosslinked thereon to form the desired gel medium layer, and then a support having the metal oxide layer thereon is provided on the gel medium layer.

The gel membrane of the invention can be employed for the horizontal or vertical electrophoresis, disc electrophoresis, etc. by known methods described, for instance, in the aforementioned texts.

The present invention will be more clearly understood with reference to the following examples.

EXAMPLE 1

A surface of a colorless transparent polyethylene terephthalate (PET) sheet (thickness 180 μm) was made hydrophilic by irradiation of ultraviolet rays. On the surface of the sheet (support) was coated a latex of vinylidene chloride-vinyl chloride (9:1) (this latex showed oxygen permeability of approx. 5 cc/m$^2$·atm·day in the form of a resinous layer of 20 μm thick.) to form an intermediate resin layer having thickness of approx. 5 μm.

The composite of the support and the resin layer showed oxygen permeability coefficient of approx. 4 cc/m$^2$·atm·day.

On the intermediate resin layer was coated a mixture of 100 ml of an aqueous gel forming solution containing 7.60 g of acrylamide, 400 mg of BIS, 1.5 ml of riboflavin (0.25 wt. % solution), 42 g of urea, 1.21 of tris(hydroxymethyl)aminomethane (CAS Registry No. 77-86-1), 0.654 g of boric acid and 75 mg of EDTA·2N, and a polymerization initiator 1.3 ml of ammonium peroxodisulfate solution (5 wt. % solution) and 33 μl of TEMED. The mixture was coated to form a layer of 0.3 mm. The coated layer was exposed for 10 min. to irradiation of high voltage mercury lamp (100 W) placed at space of 10 cm. Thus, an aqueous polyacrylamide gel membrane was formed.

COMPARISON EXAMPLE 1

The procedure of Example 1 was repeated except that the polyethylene terephthalate support was not provided with the intermediate resin layer, to form an aqueous polyacrylamide gel membrane on the support.

The polyethylene terephthalate support showed oxygen permeability coefficient of approx. 17 cc/$m^2$·atm·day

REFERENCE EXAMPLE 1

The procedure of Example 1 was repeated except that the a glass plate was employed as a support in place of the polyethylene terephthalate support provided with the intermediate resin layer, to form an aqueous polyacrylamide gel membrane on the support.

ELECTROPHORESIS TEST

At each end of the above polyacrylamide gel membranes, a sample inlet was formed. Then, each surface of the gel membranes was covered with PET film (thickness: 63 μm) to obtain a medium for electrophoresis comprising a gel membrane sandwiched between two PET films.

A DNA sample prepared by dideoxy method was electrophoresed on the polyacrylamide gel membrane for determination of base sequence. The membrane on which the sample was electrophoresed was then treated by an autoradiographic process at −80° C. for sequencing the DNA.

It was observed that electrophoresis patterns of a high resolving power were formed on the membranes of Example 1 and Reference Example 1. On the membranes of Example 1 and Reference Example 1 were respectively detected base-separated zones of 198 and 192. The electrophoresis pattern formed on the membrane of Comparison Example 1 is resolution (base-separated zones detected were 131) which is poorer than those given by the membranes of Example 1 and Reference Example 1.

EXAMPLE 2

The procedure of Example 1 was repeated except that the intermediate resin layer was replaced with a polyacrylonitrile layer (this resin showed oxygen permeability of approx. 2 cc/$m^2$·atm·day in the form of a resinous layer of 20 μm thick.) having thickness of approx. 10 μm.

The composite of the support and the resin layer showed oxygen permeability coefficient of approx. 2 cc/$m^2$·atm·day.

The aqueous polyacrylamide gel membrane was formed on the support in the same manner as in Example 1.

ELECTROPHORESIS TEST

At each end of the polyacrylamide gel membranes prepared in Example 2, Comparison Example 1 and Reference Example 1, a sample inlet was formed. Then, each surface of the gel membranes was covered with PET film (thickness: 50 μm) to obtain a medium for electrophoresis comprising a gel membrane sandwiched between two PET films.

A DNA sample prepared by Maxam-Gilbert method was electrophoresed on the polyacrylamide gel membrane for determination of base sequence. The membrane on which the sample was electrophoresed was then treated by an autoradiographic process at −80° C. for sequencing the DNA.

It was observed that electrophoresis patterns of a high resolving power were formed on the membranes of Example 2 and Reference Example 1. On the membranes of Example 2 and Reference Example 1 were respectively detected base-separated zones of 65 and 61. The electrophoresis pattern formed on the membrane of Comparison Example 1 is resolution (base-separated zones detected were 41) which was poorer than that given by the membranes of Example 2 and Reference Example 1.

EXAMPLE 3

A surface of a colorless transparent polyethylene terephthalate (PET) sheet (thickness 180 μm) was made hydrophilic by irradiation of ultraviolet rays. On the surface of the sheet (support) was coated a latex of vinylidene chloride-vinyl chloride (9:1) (this latex showed oxygen permeability of approx. 5 cc/$m^2$·atm·day in the form of a resinous layer of 20 μm thick.) to form an intermediate resin layer having thickness of approx. 5 μm.

The composite of the support and the resin layer showed oxygen permeability coefficient of approx. 4 cc/$m^2$·atm·day.

On the intermediate resin layer was coated a mixture of 100 ml of an aqueous gel forming solution containing 9.5 g of acrylamide, 0.5 g of BIS, 3.58 g of disodium hydrogenphosphate 12 hydrates, 0.33 g of sodium dihydrogenphosphate dihydrates and 0.10 g of sodium dodecylbenzenesulfate, and a polymerization initiator 1.3 ml of ammonium peroxodisulfate solution (5 wt. % solution) and 33 μl of TEMED. The mixture was coated to form a layer of 0.3 mm. The coated layer was exposed for 10 min. to irradiation of high voltage mercury lamp (100 W) placed at space of 10 cm. Thus, an aqueous polyacrylamide gel membrane was formed.

COMPARISON EXAMPLE 2

The procedure of Example 3 was repeated except that the polyethylene terephthalate support was not provided with the intermediate resin layer, to form an aqueous polyacrylamide gel membrane on the support.

The polyethylene terephthalate support showed oxygen permeability coefficient of approx. 17 cc/$m^2$·atm·day

REFERENCE EXAMPLE 2

The procedure of Example 3 was repeated except that the a glass plate was employed as a support in place of the polyethylene terephthalate support provided with the intermediate resin layer, to form an aqueous polyacrylamide gel membrane on the support.

ELECTROPHORESIS TEST

At each end of the above polyacrylamide gel membranes, a sample inlet was formed. Then, each surface of the gel membranes was covered with PET film (thickness: 63 μm) to obtain a medium for electrophoresis comprising a gel membrane sandwiched between two PET films.

A standard protein sample was electrophoresed on the polyacrylamide gel membrane for separation. The cover film was separated from the membrane on which the sample was electrophoresed. The membrane was immersed in 0.1 % aqueous solution of Coomaside Blue to dye the electrophoretically separated zone.

It was observed that electrophoresis patterns of a high resolving power were formed on the membranes of Example 3 and Reference Example 2. The electrophoresis pattern formed on the membrane of Comparison Example 2 is resolution which was poorer than that given by the membranes of Example 3 and Reference Example 2.

Moreover, smilling effects observed on the membranes of Example 3 and Reference Example 2 were less than that observed on the membrane of Comparison Example 2.

EXAMPLE 4

The procedure of Example 3 was repeated except that the intermediate resin layer was replaced with a polyacrylonitrile layer (this resin showed oxygen permeability of approx. 2 cc/m$^2$·atm·day in the form of a resinous layer of 20 μm thick.) having thickness of approx. 10 μm.

The composite of the support and the resin layer showed oxygen permeability coefficient of approx. 2 cc/m$^2$·atm·day.

The aqueous polyacrylamide gel membrane was formed on the support in the same manner as in Example 3.

ELECTROPHORESIS TEST

At the end of the polyacrylamide gel membrane of Example 4, a sample inlet was formed. Then, the surface of the gel membranes was covered with PET film (thickness: 63 μm) to obtain a medium for electrophoresis comprising a gel membrane sandwiched between two PET films.

A standard protein sample was electrophoresed on the polyacrylamide gel membrane for separation. The cover film was separated from the membrane on which the sample was electrophoresed. The membrane was immersed in 0.1 % aqueous solution of Coomasie Blue to dye the electrophoretically separated zone.

It was observed that electrophoresis pattern of a high resolving power similar to that of Example 3 was formed.

Moreover, relatively little smilling effect was observed on the membrane of Example 4, as compared with that observed on the membrane of Comparison Example 2.

We claim:

1. In a medium for electrophoresis which comprises a support of a plastic material selected from the group consisting of polyethylene terephthalate, the polycarbonate of Bisphenol A, polyvinyl chloride, vinylidene chloride-vinyl chloride copolymer, polymethyl methacrylate, polyethylene, polypropylene, cellulose acetates, and cellulose acetate propionate, and an aqueous polyacrylamide gel membrane formed by the crosslinking polymerization of an acrylamide compound and a crosslinking agent in the presence of water, the improvement which comprises a resin layer between the support and the aqueous polyacrylamide gel membrane comprising a resin having an oxygen permeability coefficient lower than that of the plastic material of the support, said coefficient being not more than 15 cc/m$^2$·atm·day when the resin is in the form of a film having a thickness of 20 μm.

2. The medium for electrophoresis as claimed in claim 1, wherein the resin layer has a thickness in the range of 0.5 to 20 μm.

3. The medium for electrophoresis as claimed in claim 1 wherein the plastic material is polyethylene terephthalate.

4. The medium for electrophoresis as claimed in claim 1, wherein the resin layer comprises at least one resin selected from the group consisting of a vinylidene chloride-vinyl chloride copolymer, polyvinyl alcohol, polyacrylonitrile, polyvinylidene chloride, a vinyl alcoholethylene copolymer, a vinylidene chlorideacrylonitrile copolymer, and an acrylonitrile-methyl acrylate-butadiene copolymer.

5. In a medium for electrophoresis which comprises a support of a plastic material selected from the group consisting of polyethylene terephthalate, the polycarbonate of Bisphenol A, polyvinyl chloride, vinylidene chloride-vinyl chloride copolymer, polymethyl methacrylate, polyethylene, polypropylene, cellulose acetates, and cellulose acetate propionate, and an aqueous polyacrylamide gel membrane formed by the crosslinking polymerization of an acrylamide compound and a crosslinking agent in the presence of water, the improvement which comprises a resin layer between the support and the aqueous polyacrylamide gel membrane comprising a resin having an oxygen permeability coefficient lower than that of the plastic material of the support, a composite of the support and the resin layer exhibiting an oxygen permeability of not more than 10 cc/m$^2$·atom·day.

6. The medium for electrophoresis as claimed in claim 5 wherein the resin layer has a thickness in the range of 0.5 to 20 μm.

7. The medium for electrophoresis as claimed in claim 5 wherein the resin layer comprises at least one resin selected from the group consisting of a vinylidene chloridevinyl chloride copolymer, polyvinyl alcohol, polyacrylonitrile, polyvinylidene chloride, a vinyl alcoholethylene copolymer, a vinylidene chloride-acrylonitrile copolymer, a vinylidene chloride-acrylonitrile copolymer, and an acrylonitrile-methyl acrylate-butadiene copolymer.

8. The medium for electrophoresis as claimed in claim 5 wherein the plastic material is polyethylene terephthalate.

* * * * *

UNITED STATES PATENT AND TRADEMARK OFFICE
CERTIFICATE OF CORRECTION

PATENT NO. : 4,897,306
DATED : January 30, 1990
INVENTOR(S) : Naohiko Sugimoto; Daijiro Nishio; Elichi Hasegawa It is certified that error appears in the above-identified patent and that said Letters Patent is hereby corrected as shown below:

ON TITLE PAGE:

Page 1, [75] Inventors:, change

"Naohiko Sugimoto; Daijiro Nishio; Elichi Hasegawa"

to

--Naohiko Sugimoto; Daijiro Nishio; Eiichi Hasegawa--

Signed and Sealed this

Twenty-sixth Day of May, 1992

Attest:

DOUGLAS B. COMER

*Attesting Officer*    *Acting Commissioner of Patents and Trademarks*